(12) United States Patent
Sardo

(10) Patent No.: US 8,802,594 B2
(45) Date of Patent: Aug. 12, 2014

(54) METHOD FOR ANTI-SPROUTING AND POSSIBLY FUNGICIDAL TREATMENT OF BULBS AND/OR TUBERS USING CLOVE OIL AND MINT OIL

(75) Inventor: Alberto Sardo, Chateaurenard (FR)

(73) Assignee: Zeda International, Saint Andiol (FR)

( * ) Notice: Subject to any disclaimer, the term of this patent is extended or adjusted under 35 U.S.C. 154(b) by 0 days.

(21) Appl. No.: 13/577,647

(22) PCT Filed: Feb. 7, 2011

(86) PCT No.: PCT/FR2011/050239
§ 371 (c)(1),
(2), (4) Date: Dec. 4, 2012

(87) PCT Pub. No.: WO2011/095751
PCT Pub. Date: Aug. 11, 2011

(65) Prior Publication Data
US 2013/0072383 A1 Mar. 21, 2013

(30) Foreign Application Priority Data
Feb. 8, 2010 (FR) ..................................... 10 50863

(51) Int. Cl.
*A01N 35/06* (2006.01)
*A01P 21/00* (2006.01)
*A01P 3/00* (2006.01)
*A01N 65/00* (2009.01)
*A01N 65/28* (2009.01)

(52) U.S. Cl.
CPC ................. *A01N 65/00* (2013.01); *A01N 65/28* (2013.01); *A01N 35/06* (2013.01)
USPC ...................................................... 504/118

(58) Field of Classification Search
CPC ... A01N 65/00; A01N 65/28; A01N 2300/00; A01N 25/00; A01N 31/16; A01N 65/22
USPC ...................................................... 504/118
See application file for complete search history.

(56) References Cited

U.S. PATENT DOCUMENTS

| 5,811,372 A | 9/1998 | Riggle et al. | |
|---|---|---|---|
| 8,329,618 B1 * | 12/2012 | Schafer et al. | 504/189 |
| 2005/0019269 A1 * | 1/2005 | Marks et al. | 424/45 |

FOREIGN PATENT DOCUMENTS

| EP | 0719499 A1 | 7/1996 |
|---|---|---|
| EP | 1052905 B1 | 2/2004 |
| EP | 1790225 A1 | 5/2007 |
| FR | 2863825 A1 | 6/2005 |
| FR | 2923355 A1 | 5/2009 |
| FR | 2923356 A1 | 5/2009 |
| WO | 200032063 A1 | 6/2000 |

OTHER PUBLICATIONS

PACE International, "Biox-Combo, Material Safety Data Sheet", dated Jan. 12, 2008, retrieved from the internet on Jul. 29, 2010, XP007914193.
PACE International, "Biox-EC Natural Sprout Inhibitors, 15EC & Biox-40EC", dated Jan. 1, 2009, retrieved from the internet on Jul. 28, 2010, XP007914183.
PACE International, "Biox-COMBO, Liquid CIPC/Clove Oil Combination Potato Sprout Inhibitor by Thermofogging", dated Jan. 1, 2009, retrieved from the internet on Jul. 28, 2010; XP007914185.
PACE International, "Biox-M, Material Safety Data Sheet", dated Jan. 6, 2009, retrieved from the internet on Jul. 28, 2010, XP007914191.
PACE International, "Biox-C Organic Potato Sprout Inhibitor applied by Thermofogging", dated Jan. 1, 2009, retrieved from the internet on Jul. 28, 2010, XP007914184.
Kleinkopf, G.E., et al., "Alternative Sprout Suppressants for Stored Potatoes", dated Jan. 23, 2002, retrieved from the Internet on Jul. 28, 2010, XP009136988.
Frazier, M.J., et al., "Orgnic and Alternative Methods for Potato Sprout Control in Storage", dated Sep. 1, 2004, retrieved from the Internet on Jul. 28, 2010, XP007914188.
Kleinkopf, G.E., et al., "Sprout Inhibition in Storage: Current Status, New Chemistries and Natural Compounds", pp. 317-327, dated Mar. 1, 2003, American Journal of Potato Research, Orono, ME, USA., vol. 80, XP007914187.
De Carvalho, Carla C.C.R., et al., "Carvone: Why and How Should One Bother to Produce This Terpene", pp. 413-422, dated Apr. 1, 2006, Food Chemistry, Elsevier Ltd., NL vol. 95, XP007914186.
International search report for application No. PCT/FR2011/050239 dated May 9, 2011.

* cited by examiner

*Primary Examiner* — Janet Epps-Smith
*Assistant Examiner* — Courtney Brown
(74) *Attorney, Agent, or Firm* — Patterson & Sheridan, L.L.P.

(57) ABSTRACT

The invention concerns a method for anti-sprouting and possible fungicidal treatment of bulbs and/or tubers comprising simultaneous, separate or time-staggered applications to the said bulbs and/or tubers of:
eugenol and/or clove oil, and
L-carvone and/or mint oil.

9 Claims, 3 Drawing Sheets

Figure 1:
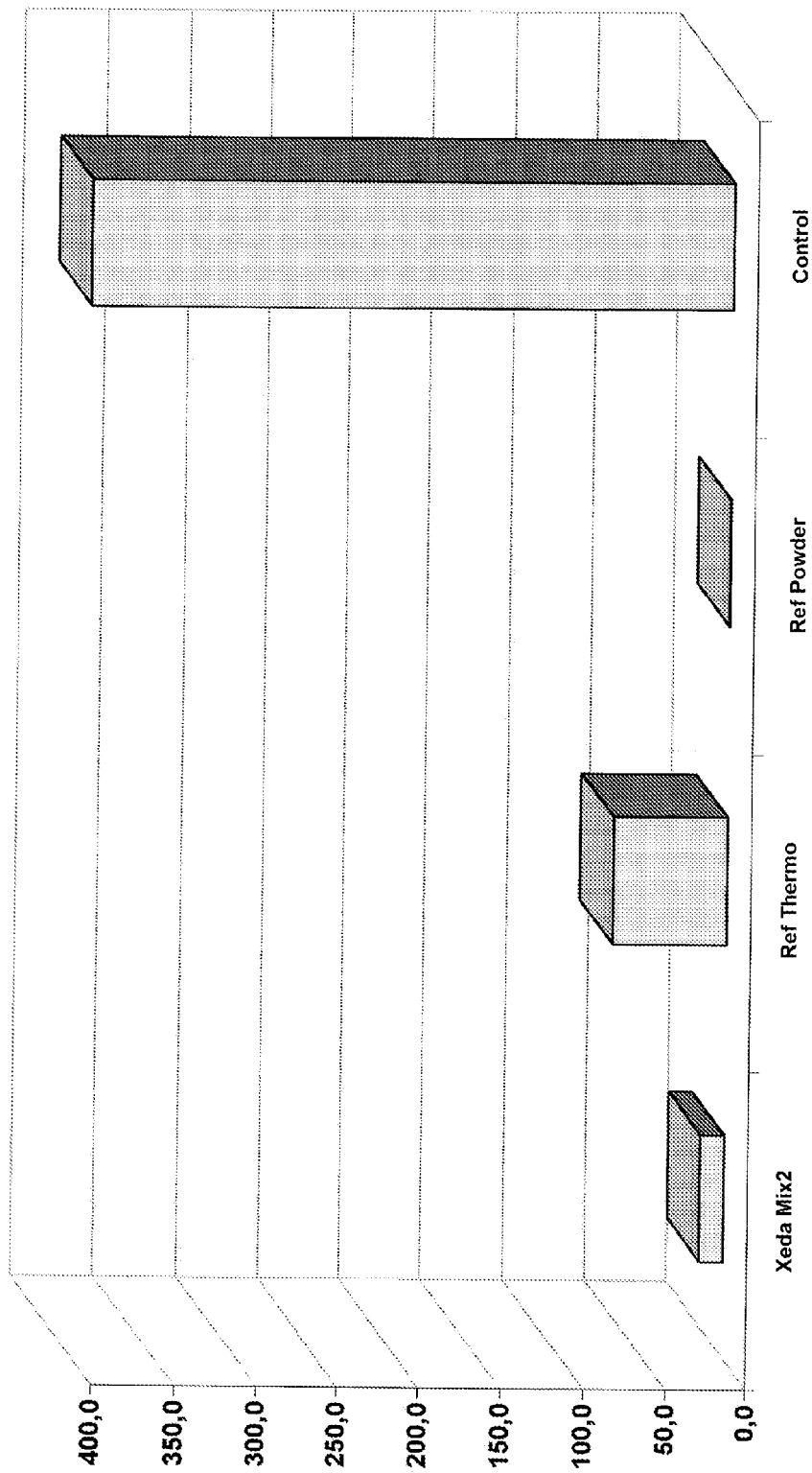

METHOD FOR ANTI-SPROUTING AND POSSIBLY FUNGICIDAL TREATMENT OF BULBS AND/OR TUBERS USING CLOVE OIL AND MINT OIL

The present invention concerns a method for anti-sprouting and possible fungicidal treatment of bulbs and/or tubers comprising the application to the said bulbs and/or tubers of a combination of clove oil and mint oil.

This method is particularly suitable for the treatment of onion bulbs and potato tubers.

After harvesting potatoes or other tubers these are stored at temperatures of the order of 20 to 30° C. for about 10 days to harden their periderm layer or "skin", and are then gradually cooled down to their storage temperature which is about 10° C., generally between 7 and 10° C.

During the first and second months following after their harvesting, the tubers remain in the dormant state and have little tendency to germinate.

However, before the end of this period, the tubers must be chemically treated to inhibit germination which would be responsible for harmful effects, such as loss of fresh weight, conversion of starch to sugars and a reduction in the quality of the tubers and deterioration of their appearance.

Bulbs are normally stored at lower temperatures but this does not prevent risks of germination especially when they are brought back to ambient temperature.

The sprout-inhibiting treatment methods most frequently applied use chemical agents such as chloropropham (CIPC 1-methylethyl-3-chlorophenylcarbamate). These chemical agents carry high toxicity risks for the consumer, which means that authorized doses are constantly being reduced. On this account, research has essentially focused on the development of alternative products.

Application FR 2 891 438 describes a method for the sprout-inhibiting treatment of bulbs and/or tubers by applying a composition comprising eugenol in particular and/or clove oil. Clove oil contains eugenol.

Application FR 2 886 516 reports that eugenol has biocide action against fungi and bacteria.

Applications FR 2 728 142, FR 2 923 356 and WO 00/32054 describe a composition for the sprout-inhibiting treatment of bulbs and/or tubers particularly comprising L-carvone and/or mint oil. L-carvone can be obtained from natural sources, particularly from common mint (*Mentha spicata*).

Applications EP 0 795 272, FR 2 923 355 and FR 2 923 356 describe a fungicidal treatment method for bulbs and/or tubers by applying a composition comprising L-carvone in particular.

Nevertheless, no alternative product exhibits activity greater than that of CIPC.

It is one of the objectives of the present invention to provide a sprout-inhibiting and optionally fungicidal treatment for bulbs and/or tubers having stronger activity than CIPC whilst being less toxic than CIPC.

The subject of the invention is therefore a sprout-inhibiting treatment for bulbs and/or tubers comprising the simultaneous, separate or time-staggered applications to the said tubers and/or tubers of a combination:
of eugenol and/or clove oil, and
L-carvone and/or mint oil,
the said combination comprising:
from 1% to 99% by weight of eugenol, and
from 1% to 99% by weight of L-carvone.

The invention is based on the unexpected discovery that the combined application of eugenol and/or clove oil and of L-carvone and/or mint oil allows the more efficient prevention of the germination of bulbs and tubers and/or better decontaminates and/or better protects against contamination than a composition comprising eugenol and/or clove oil or a composition comprising L-carvone and/or mint oil. More specifically, the method of the invention allows a synergic sprouting-inhibiting effect of its constituents to be obtained.

Clove oil generally contains from 70 to 95% by weight of eugenol, in particular from 80 to 92%, typically from 88 to 90% by weight of eugenol. Mint oil generally comprises from 50 à 80% by weight of L-carvone, typically of the order of 70%. The adapted corresponding weight proportions of mint oil and clove oil can easily be calculated by persons skilled in the art taking into account the L-carvone and eugenol contents of these oils.

Mint oil alone and/or L-carvone have anti-sprouting activity of great interest and comparable with the reference product (CIPC). The anti-sprouting activity of clove oil alone is lower than that of mint oil or CIPC. It was therefore not obvious that the combination of mint oil and/or L-carvone and of eugenol and/or clove oil could allow a level of sprouting inhibition to be reached that is higher than that of CIPC.

In addition, clove oil has an unpleasant, persistent odour due to its eugenol content, which did not prompt the simultaneous or separate application of eugenol and/or clove oil and of L-carvone and/or mint oil. Yet the inventors have discovered that the odour of mint oil, even though gentler than the odour of clove oil, covers the odour of clove oil in fully satisfactory manner particularly at a mint oil concentration reaching 10% of the mixture.

According to one particularly advantageous embodiment, the anti-sprouting method of the invention allows fungicidal treatment in addition to the sprout-inhibiting effect. Therefore, the said anti-sprouting method additionally provides fungicidal treatment. This is of particular interest since the activity spectra of eugenol (or clove oil) and of L-carvone (or mint oil) together allow the coverage of all fungi generally affecting bulbs and tubers. Mint oil has displayed fungicidal activity against *Helminthosporium solani* and *Rhizoctonia solani* whilst clove oil has displayed fungicidal activity against various *Phytophtora* and *Fusaria*. In addition, clove oil has a very distinct bactericidal effect against bacteria such as *Erwinia Carotovora* which frequently attacks potatoes.

In one embodiment, the method comprises the simultaneous, separate or time-staggered applications to the said bulbs and/or tubers of:
clove oil, and
mint oil.

The mint and clove oils are preferably used pure i.e. without the addition of a solvent or additive.

In another embodiment, the method comprises the simultaneous; separate or time-staggered application to the said bulbs and/or tubers of:
eugenol, and
L-carvone.

In the method of the invention, the applications of eugenol and/or clove oil and of L-carvone and/or mint oil can be simultaneous.

The combination comprises:
from 1% to 99% by weight of eugenol, and
from 1% to 99% by weight of L-carvone.

Typically, the applied combination comprises:
from 45% to 85% by weight of eugenol, and
from 15% to 55% by weight of L-carvone.

Preferably, the applied combination comprises:
from 60% to 70% by weight of eugenol, and
from 30 to 40% by weight of L-carvone.

The term <<combination>> used in the present application refers to a simultaneous, separate or time-staggered application of the constituent ingredients.

The corresponding adapted weight proportions of mint oil and clove oil can easily be calculated by persons skilled in the art taking into account the L-carvone and eugenol contents of the oils, such as recalled above, and/or the concentration of the oils used.

In the method of the invention, a combination is generally applied:

at an initial total dose of L-carvone and eugenol of 35 to 120 g per tonne of bulbs and/or tubers, then
at total doses of L-carvone and eugenol of 20 to 90 g per tonne of bulbs and/or tubers at frequencies of between 15 and 90 days.

The total dose of L-carvone and eugenol corresponds to the accumulated doses of L-carvone and eugenol.

The corresponding adapted doses of mint oil and clove oil can easily be calculated by persons skilled in the art taking into account the oil contents of L-carvone and eugenol such as recalled above and/or the concentration of the oils used.

In the method of the invention, the applications of eugenol and/or clove oil and of L-carvone and/or mint oil can also be applied at separate times. Each above-mentioned dose is then applied in two operations (eugenol then L-carvone, or the reverse). According to one particularly advantageous embodiment, the eugenol and/or clove oil and the L-carvone and/or mint oil are applied simultaneously.

The eugenol and/or clove oil, and the L-carvone and/or mint oil can be applied to the tubers and/or bulbs using any of the methods known in the art, in particular by atomization or thermal fogging. Preferably the application uses thermal fogging. This technique is known per se. It can advantageously be applied using the Electrofog Xeda device or any other device such as described in application FR 2 566 681.

The suitable temperatures for thermal fogging are between 170° C. and 235° C., in particular between 190° C. and 215° C. At these temperatures a good quality fog is obtained (i.e. composed of small size particles of small size distribution) which allows very homogeneous distribution of eugenol and/or clove oil and of L-carvone and/or mint oil over the bulbs and/or tubers.

Preferably the tubers are potatoes; the bulbs are onions, garlic, shallots or flower bulbs.

The invention will be better understood in the light of the following figures and examples.

Figure 2:
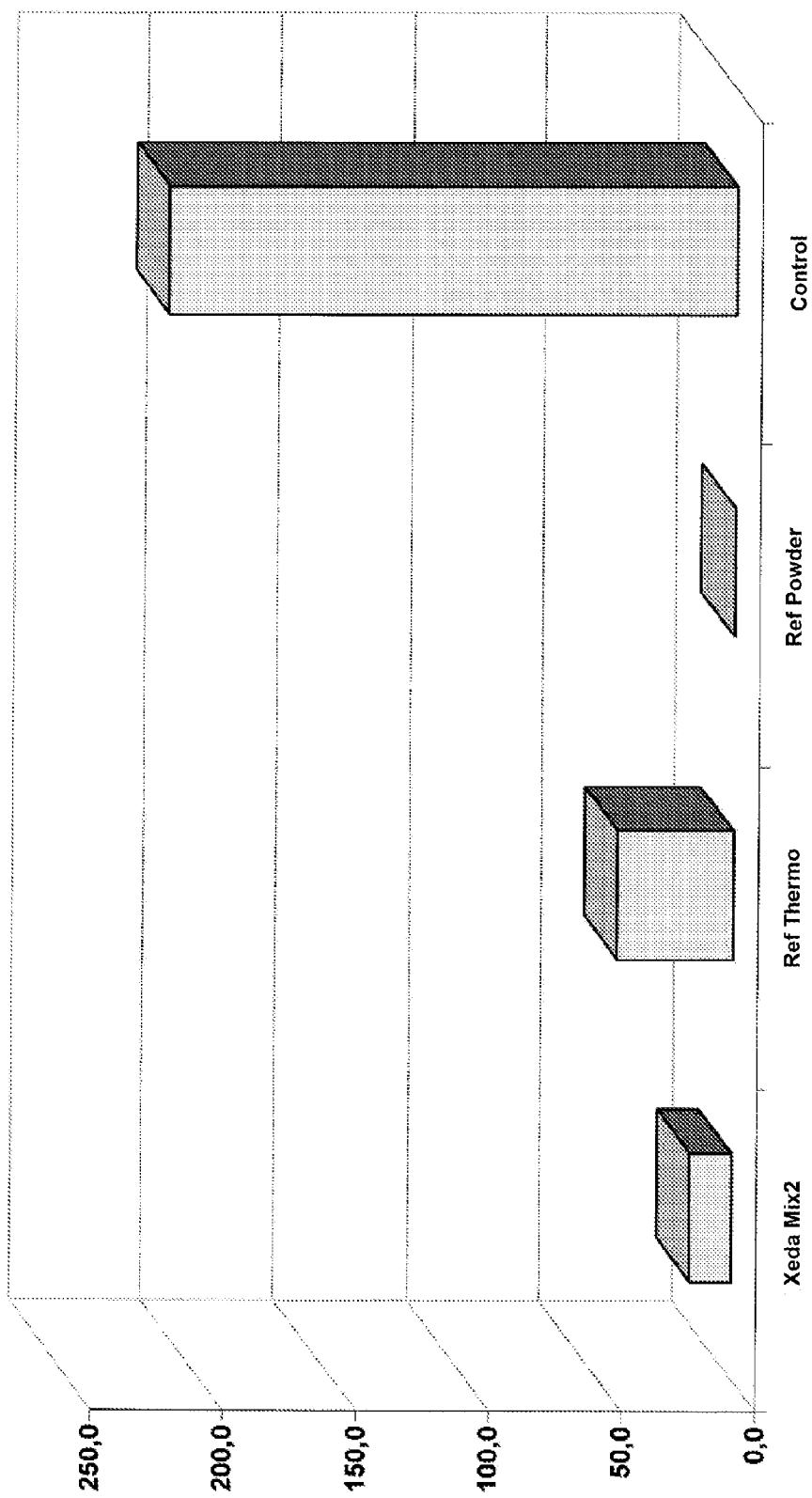
Figure 3:
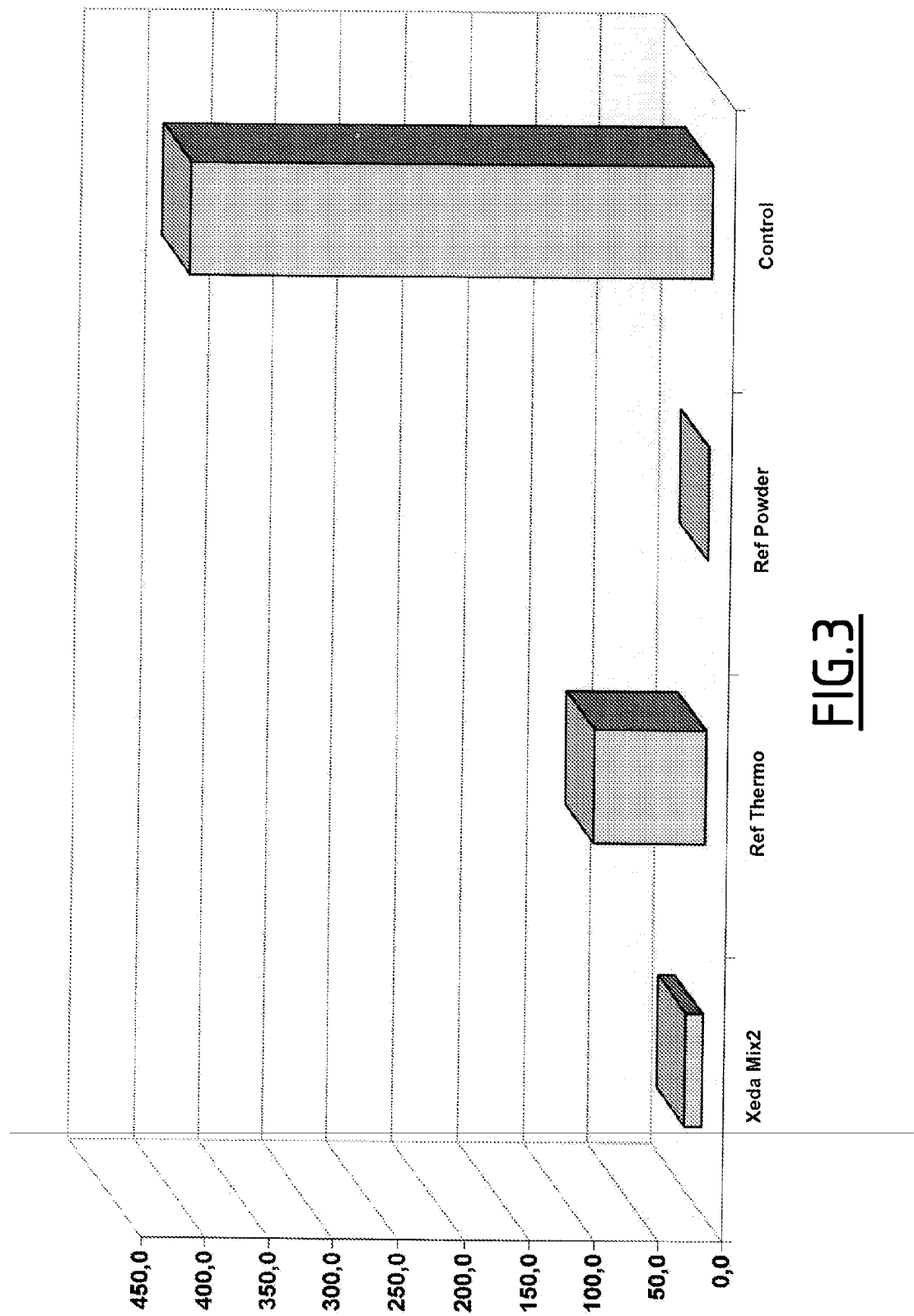

FIGS. 1 to 3 illustrate the sprout weights (in g of sprouts per 10 kg of potatoes) for Bintje (FIG. 1), Nicola (FIG. 2) and Charlotte potatoes (FIG. 3) subjected to the anti-sprouting treatments of Example 2 and held in storage for 6 months.

EXAMPLE 1

Evidencing of the Synergic Effect Between Clove Oil and Mint Oil

The sprout-inhibiting treatments were carried out over a 6-month period.

The mint oil used contained about 70% L-carvone and the clove oil used contained about 90% eugenol.

The tested potatoes were Bintje, Nicola and Charlotte varieties.

An anti-sprouting composition A consisting of a mixture of clove oil (supplied by Charabot (Grasse)/mint oil (supplied by Charabot (Grasse) at 2:1 v/v was prepared. The densities of mint and clove are respectively 0.94 and 1.04. This composition was applied to the potatoes using Electrofog Xeda 3000 equipment at an output temperature of 210° C., at an initial dose of 90 grams of composition per tonne of potatoes,
at subsequent doses of 30 grams of composition per tonne of potatoes every three weeks.

For comparison, some potatoes were treated:

B: either with mint oil alone
at an initial dose of 90 grams of mint oil per tonne of potatoes,
at subsequent doses of 30 grams of mint oil per tonne of potatoes every three weeks;
C: or with clove oil alone
at an initial dose of 90 grams of clove oil per tonne of potatoes,
at subsequent doses of 30 grams of clove oil per tonne of potatoes every three weeks;
D: or with CIPC (Xedamate Aerosol 88 containing 20% CIPC) by thermal fogging:
at an initial dose of 60 grams of Xedamate Aerosol 88 per tonne of potatoes,
at subsequent doses of 30 grams of Xedamate Aerosol 88 per tonne of potatoes every 60 days;
E: or with CIPC (Neoconserviet by Agriphyt) (formulation with 1% CIPC) dusted on harvesting applied at a dose of 625 grams per tonne of potatoes.

For reference, one stock of potatoes was not subjected to any sprout-inhibiting treatment (F) (control).

The germination indexes (%) of the potatoes are grouped together in following Table 1.

TABLE 1

Sprout weights expressed as g/10 kg of potatoes as per potato variety and the applied anti-sprouting treatment.

| | Composition | Sprout weights Bintje | Sprout weights Nicola | Sprout weights Charlotte |
|---|---|---|---|---|
| A | 2/3 clove oil + 1/3 mint oil | 14.0 | 15.0 | 13.0 |
| B | mint oil | 40.0 | 35.0 | 40.0 |
| C | clove oil | 150.0 | 130.0 | 110.0 |
| D | 20% CIPC formulation | 71.0 | 42.0 | 70.0 |
| E | 1% CIPC powder formulation | 0.0 | 0.0 | 0.0 |
| | Control | 416.0 | 215.0 | 380.0 |

These results evidence a synergic effect when clove oil and mint oil are used simultaneously. The combination of clove oil and mint oil allows much more efficient prevention of bulb or tuber germination than clove oil or mint oil used alone.

Under the test conditions, the composition is about three times more efficient than the CIPC formulation applied using thermal fogging.

The results are similar for the three tested potato varieties.

EXAMPLE 2

Influence of Frequency of Treatment

The anti-sprouting treatments were conducted over a period of 6 months.

The mint oil used contained about 70% of L-carvone and the clove oil used contained about 90% of eugenol.

The tested potatoes were Bintje, Nicola and Charlotte varieties.

A sprout-inhibiting composition was prepared consisting of a 2:1 v/v mixture of clove oil (supplied by Charabot [Grasse])/mint oil (supplied by Charabot [Grasse]).

To reduce the frequency of operations whilst maintaining the same quantities globally used in Example 1, the composition was applied to potatoes using Electrofog Xeda 3000 equipment at an output temperature of 210° C., at an initial dose of 90 grams of composition per tonne of potatoes, at subsequent doses of 60 grams of composition per tonne of potatoes every six weeks (<<Xeda Mix2>> in FIGS. 1 to 3).

For comparison, some potatoes were treated:

either with CIPC (Xedamate Aerosol 88 containing 20% CIPC) by thermal fogging:

at an initial dose of 60 grams of Xedamate Aerosol 88 per tonne of potatoes, at subsequent doses of 30 grams of Xedamate Aerosol 88 per tonne of potatoes every 2 months (<<Ref Thermo>> in FIGS. 1 to 3);

or with CIPC (Neoconserviet by Agriphyt) (1% CIPC formulation) applied by dusting at a dose of 625 grams per tonne of potatoes on harvesting (<<Ref Powder>> in FIGS. 1 to 3).

For reference, a stock of potatoes was not subjected to sprout-inhibiting treatment (control in FIGS. 1 to 3).

Sprout weights (in g of sprouts per 10 kg of potatoes) for the potatoes are given in FIGS. 1 to 3, FIG. 1 corresponding to the Bintje variety, FIG. 2 corresponding to the Nicola variety and FIG. 3 to the Charlotte variety.

Under the test conditions, the composition is about three times more efficient than the CIPC formulation applied by thermal fogging.

The sprout-inhibiting effect of the clove oil/mint oil composition is similar that of the clove oil/mint oil composition in Example 1, which shows that the increased time interval between applications of the composition (60 days in Example 2 and 30 days in Example 1) is of no consequence.

The results are similar for the three tested potato varieties.

EXAMPLE 3

Content of the Composition in Treated Potatoes

The residual contents were measured of L-carvone (derived from the mint oil) and eugenol (derived from the clove oil) in the various varieties of potatoes (peeled or unpeeled) treated with the clove oil/mint oil combination following the application conditions of Example 2 (Table 2: eugenol and Table 3: L-carvone).

TABLE 2

Eugenol content of potatoes treated with a 2:1 v/v clove oil/mint oil combination.

|  | Treatment time | Variety | Eugenol content (mg/Kg) |
|---|---|---|---|
| Unpeeled potatoes | 6 months | Nicola | 0.38 |
|  |  | Monalisa | 0.19 |
|  |  | Bintje | 0.40 |
|  |  | Charlotte | 0.32 |
|  |  | Agata | 0.22 |
|  |  | Roseval | 0.36 |
|  | 9 months | Nicola | 0.47 |
|  |  | Monalisa | 0.24 |
|  |  | Bintje | 0.28 |
|  |  | Agata | 0.37 |
| Peeled potatoes | 6 months | Nicola | 0.03 |
|  |  | Monalisa | <0.02 |
|  |  | Bintje | <0.02 |
|  |  | Charlotte | <0.02 |
|  |  | Agata | <0.02 |
|  |  | Roseval | <0.02 |
|  | 9 months | Nicola | <0.02 |
|  |  | Monalisa | <0.02 |
|  |  | Bintje | <0.02 |
|  |  | Agata | <0.02 |

TABLE 2

L-carvone content of potatoes treated with a 2:1 v/v clove oil/mintoil combination

|  | Treatment time | Variety | L-carvone content (mg/Kg) |
|---|---|---|---|
| Unpeeled potatoes | 6 months | Nicola | 0.20 |
|  |  | Monalisa | 0.16 |
|  |  | Bintje | 0.34 |
|  |  | Charlotte | 0.18 |
|  |  | Agata | 0.23 |
|  |  | Roseval | 0.317 |
|  | 9 months | Nicola | 0.16 |
|  |  | Monalisa | 0.23 |
|  |  | Bintje | 0.07 |
|  |  | Agata | 0.09 |
| Peeled potatoes | 6 months | Nicola | <0.02 |
|  |  | Monalisa | <0.02 |
|  |  | Bintje | <0.02 |
|  |  | Charlotte | <0.02 |
|  |  | Agata | <0.02 |
|  |  | Roseval | <0.02 |
|  | 9 months | Nicola | 0.02 |
|  |  | Monalisa | <0.02 |
|  |  | Bintje | <0.02 |
|  |  | Agata | <0.02 |

The invention claimed is:

1. A method for anti-sprouting treatment of bulbs and/or tubers, comprising simultaneous, separate or time-staggered applications to the said bulbs and/or tubers of a combination consisting of:
   eugenol and/or clove oil, and
   L-carvone and/or mint oil,
   the said combination consisting of:
   from 1% to 99% by weight of eugenol, and
   from 1% to 99% by weight of L-carvone.

2. The method according to claim 1 wherein the applied combination consists of:
   from 45% to 85% by weight of eugenol, and
   from 15% to 55% by weight of L-carvone.

3. The method according to claim 2 wherein the applied combination consists of:
   from 60% to 70% by weight of eugenol, and
   from 30% to 40% by weight of L-carvone.

4. The method according to claim 1 wherein a combination is applied:
   at an initial total dose of L-carvone and eugenol of 35 to 120 g per tonne of bulbs and/or tubers, then
   at total doses of L-carvone and eugenol of 20 to 90 g per tonne of bulbs and/or tubers at frequencies of between 15 and 90 days.

5. The method according to claim 1 wherein the applications are carried out by thermal fogging.

6. The method according to claim 5 wherein thermal fogging is conducted at a temperature of between 170° C. and 235° C.

7. The method according to claim 6 wherein thermal fogging is conducted at a temperature of between 190° C. and 215° C.

8. The method according to claim 1 wherein the tubers are potatoes and the bulbs are onions, garlic, shallots or flower bulbs.

9. The method according to claim 1 such that the said anti-sprouting treatment additionally allows fungicidal treatment.

* * * * *